US010258297B2

(12) United States Patent
Teshigawara

(10) Patent No.: US 10,258,297 B2
(45) Date of Patent: Apr. 16, 2019

(54) MEDICAL DIAGNOSTIC-IMAGING APPARATUS

(71) Applicant: Toshiba Medical Systems Corporation, Otawara-shi (JP)

(72) Inventor: Manabu Teshigawara, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 16 days.

(21) Appl. No.: 15/591,494

(22) Filed: May 10, 2017

(65) Prior Publication Data
US 2017/0325756 A1 Nov. 16, 2017

(30) Foreign Application Priority Data

May 12, 2016 (JP) .................. 2016-096473
May 8, 2017 (JP) .................. 2017-092608

(51) Int. Cl.
*A61B 6/03* (2006.01)
*A61B 6/00* (2006.01)
(Continued)

(52) U.S. Cl.
CPC ............ *A61B 6/037* (2013.01); *A61B 6/4241* (2013.01); *A61B 6/4258* (2013.01); *A61B 6/585* (2013.01); *G01T 1/1647* (2013.01); *G01T 1/208* (2013.01); *G01T 1/2018* (2013.01); *G01T 1/40* (2013.01); *H04N 5/32* (2013.01)

(58) Field of Classification Search
CPC ............................. G01T 1/2985; A61B 6/037
See application file for complete search history.

(56) References Cited

U.S. PATENT DOCUMENTS 4,866,615 A   9/1989  Ichihara
6,175,118 B1 * 1/2001  Takayama ............ G01T 1/1642
                                                            250/363.07
(Continued)

FOREIGN PATENT DOCUMENTS

JP        62-43584      2/1987
JP        2014-176620   9/2014
WO     WO 2007/043137 A1  4/2007

*Primary Examiner* — Michael C Bryant
(74) *Attorney, Agent, or Firm* — Oblon, McClelland, Maier & Neustadt, L.L.P.

(57) ABSTRACT

A medical diagnostic-imaging apparatus of an embodiment includes plural converters and processing circuitry. The converters output an electrical signal based on an incident radioactive ray. The processing circuitry identifies a first signal intensity that is a signal intensity corresponding to a peak of the number of the radioactive rays based on a relationship between a signal intensity of an electrical signal output from the convertor and the number of incident radioactive rays, for each of the converters. The processing circuitry identifies a second signal intensity that is a signal intensity corresponding to energy of a radioactive ray that has entered therein without scattering, based on a relationship between the signal intensity and the number of radioactive rays in a higher intensity than the first signal intensity. The processing circuitry corrects a signal intensity of an electrical signal that is output from the respective converters such that the second signal intensity identified for each of the converters matches with a target signal intensity.

14 Claims, 10 Drawing Sheets

(51) Int. Cl.
  *G01T 1/164*   (2006.01)
  *G01T 1/20*    (2006.01)
  *G01T 1/208*   (2006.01)
  *G01T 1/40*    (2006.01)
  *H04N 5/32*    (2006.01)

(56) References Cited

U.S. PATENT DOCUMENTS

| | | |
|---|---|---|
| 2009/0179154 A1 | 7/2009 | Ooi |
| 2013/0223587 A1* | 8/2013 | Moriyasu ................ A61B 6/03 378/5 |
| 2015/0327827 A1 | 11/2015 | Teshigawara |

* cited by examiner

FIG.2

| MODULE ID | SCINTILLATOR NUMBER (P) | ENERGY VALUE (E) | DETECTION TIME (T) |
|---|---|---|---|
| D1 | P11 | E11 | T11 |
| | P12 | E12 | T12 |
| | P13 | E13 | T13 |
| | ⋮ | ⋮ | ⋮ |

| MODULE ID | SCINTILLATOR NUMBER (P) | ENERGY VALUE (E) | DETECTION TIME (T) |
|---|---|---|---|
| D2 | P21 | E21 | T21 |
| | P22 | E22 | T22 |
| | P23 | E23 | T23 |
| | ⋮ | ⋮ | ⋮ |

| MODULE ID | SCINTILLATOR NUMBER (P) | ENERGY VALUE (E) | DETECTION TIME (T) |
|---|---|---|---|
| D3 | P31 | E31 | T31 |
| | P32 | E32 | T32 |
| | P33 | E33 | T33 |
| | ⋮ | ⋮ | ⋮ |

| COINCI-DENCE NO. | SCINTILLATOR NUMBER (P) | ENERGY VALUE (E) | DETECTION TIME (T) | SCINTILLATOR NUMBER (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

MEDICAL DIAGNOSTIC-IMAGING APPARATUS

CROSS-REFERENCE TO RELATED APPLICATIONS

This application is based upon and claims the benefit of priority from Japanese Patent Application No. 2016-096473, filed on May 12, 2016; and Japanese Patent Application No. 2017-092608, filed on May 8, 2017; the entire contents of which are incorporated herein by reference.

FIELD

Embodiments described herein relate generally to a medical diagnostic-imaging apparatus.

BACKGROUND

Conventionally, as a medical diagnostic-imaging apparatus that can perform diagnosis of a function of a living body tissue of a subject, a positron emission computed tomography (PET) apparatus, a single photon emission computed tomography (SPECT) apparatus, and the like have been known.

A detector module, which is a gamma ray detector, in a PET apparatus receives, by a photomultiplier tube (PMT), a scintillation photon that is emitted when a gamma ray radiated from a subject enters a scintillator, and converts it into an electrical signal. For example, one scintillation photon that collides against a photoelectric surface of the photomultiplier tube emits one photon by the photoelectric effect. In a stage subsequent to the photoelectric surface, multiple dynodes that are positively charged are arranged. To these multiple dynodes, the photon accelerated by electric attraction travels, and collides with the dynodes. When the photon collides with the dynodes, several millions of photons are output as electrical signals from the photomultiplier tube. That is, a single photon put out from a single scintillation photon is multiplied to several millions of photons to flow as electrical signals. The multiplication factor of the number of photons at this time is called gain factor. This gain factor varies among photomultiplier tubes. For example, variations in the gain factor can range several-fold.

Accordingly, output currents vary according to a photomultiplier tube even if the same number of scintillation photons enter the photomultiplier tubes. Therefore, to express energy of an incident gamma ray by the scintillation photon, it is necessary to perform calibration, namely, energy calibration to make the output of the photomultiplier tubes uniform by amplifier circuitry in a later stage.

Therefore, it has generally been practiced that gamma rays are input to a detector module from a shielded discrete radio source or a shielded linear radio source by using a shielded discrete radio source or a shielded linear radio source of 68 Ge, or the like that radiates little-scattering monochromatic gamma rays with small dispersion, and a histogram of a time integral value of an output signal is generated to adjust the amplification factor in the amplifier circuitry so that peak positions are substantially consistent in all of the photomultiplier tubes.

BRIEF DESCRIPTION OF THE DRAWINGS

FIG. 2 is a diagram for explaining a list of counting data according to the first embodiment;

FIG. 3 is a diagram for explaining a chronological list of simultaneous counting data according to the first embodiment;

DETAILED DESCRIPTION

A medical diagnostic-imaging apparatus of an embodiment includes multiple converters and processing circuitry. The converters output an electrical signal based on an incident radioactive ray. The processing circuitry identifies a first signal intensity that is a signal intensity corresponding to a peak of the number of radioactive rays based on a relationship between a signal intensity of the electrical signal output from the converter and the number of incident radioactive rays, for each of the converters. The processing circuitry identifies a second signal intensity that is a signal intensity corresponding to energy of a radioactive ray that has entered therein without scattering, based on a relationship between the signal intensity and the number of the radioactive rays in a higher intensity than the first signal intensity. The processing circuitry corrects a signal intensity of an electrical signal that is output from each of the converters so that the second signal intensity that is identified for each of the converters matches with a target signal intensity.

Embodiments of a medical diagnostic-imaging apparatus are explained in detail below with reference to the accompanying drawings. The respective embodiments can be combined appropriately.

First Embodiment

First, a configuration of a nuclear-medical imaging apparatus as a medical diagnostic-imaging apparatus according to a first embodiment is explained. In the first embodiment, as one example of the nuclear-medical imaging apparatus, a PET apparatus is explained.

Figure 1:
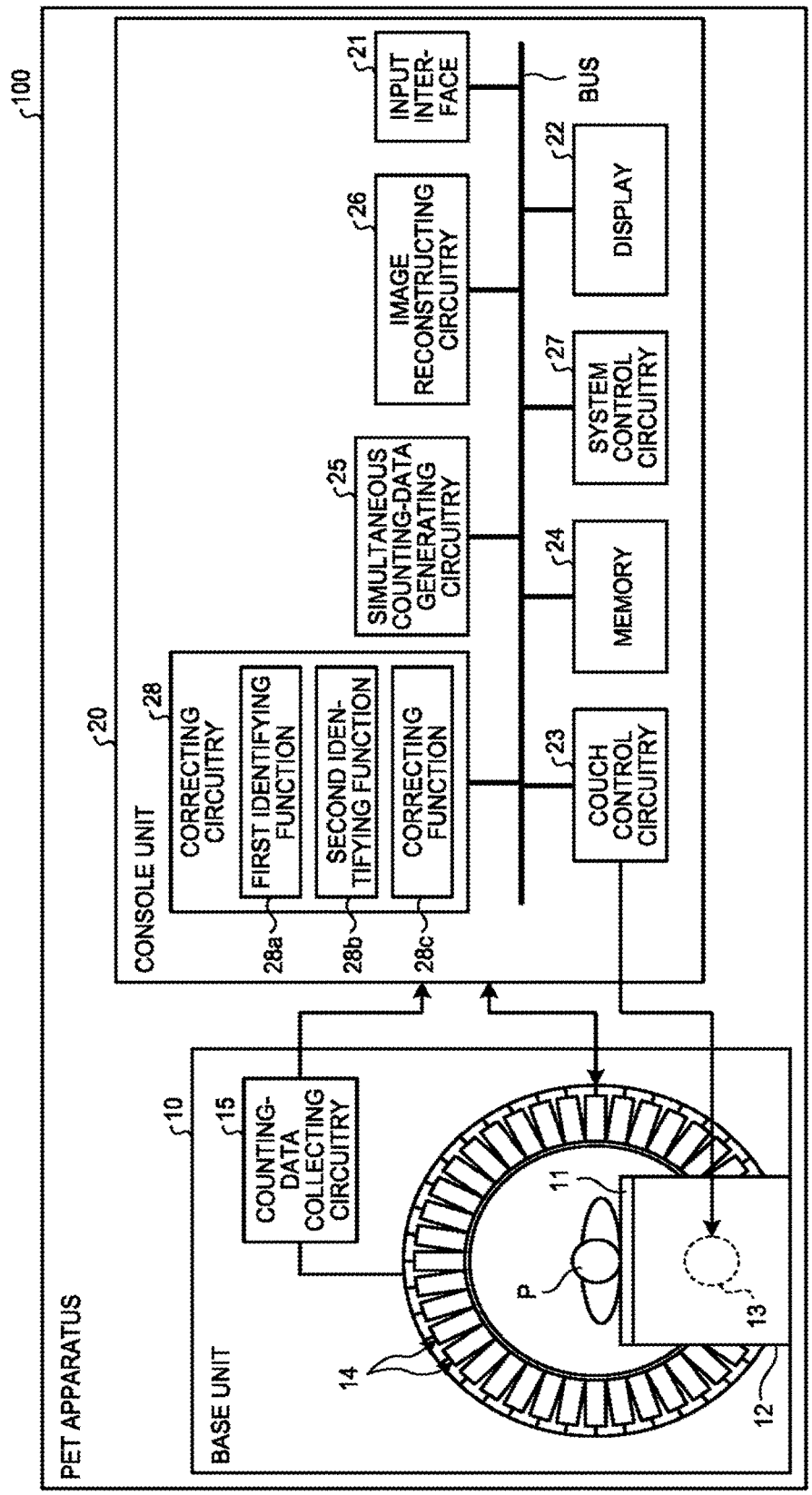
FIG. 1 shows one example of a configuration of a PET apparatus according to a first embodiment.

FIG. 1 shows one example of a configuration of a PET apparatus 100 according to the first embodiment. As shown in FIG. 1, the PET apparatus 100 according to the embodiment includes a base unit 10 and a console unit 20.

The base unit 10 detects a pair of gamma rays (pair-annihilation gamma ray) that is output when a positron emitted inside a subject P is coupled with an electron and pair-annihilated by a detector module that is arranged to surround the subject P in a ring form, and generates counting data from an output signal (electrical signal) of a detector module 14, thereby collecting the counting data. To the subject P, for example, a radioactive medical product that is marked by a positron emission nuclide is given. Note that gamma ray is one example of the radioactive ray.

As shown in FIG. 1, the base unit 10 includes a top plate 11, a couch 12, couch driving circuitry 13, the multiple detector modules 14, and counting-data collecting circuitry 15. The base unit 10 has a hollow to be an imaging opening as shown in FIG. 1.

The top plate 11 is a couch on which the subject P is placed, and is arranged on the couch 12. The couch driving circuitry 13 moves the top plate 11 under control of a couch control circuitry 23 described later. For example, the couch driving circuitry 13 moves the subject P into the imaging opening of the base unit 10 by moving the top plate 11.

The detector module 14 detects a pair of gamma rays that is emitted when a positron emitted inside the subject P is coupled with an electron and pair-annihilated, and outputs an electrical signal based on the detected pair of gamma rays. As shown in FIG. 1, the multiple units of the detector modules 14 are arranged so as to surround the subject P in a ring form. The detector module 14 converts the gamma ray emitted from the subject P into light, and converts the obtained light into an electrical signal. A configuration of the detector module 14 is described later.

The counting-data collecting circuitry 15 generates counting data from an output signal of the detector module 14, and stores the generated counting data in a memory 24 described later. For example, the counting-data collecting circuitry 15 is implemented by a processor.

For example, the counting-data collecting circuitry 15 collects counting data by generating counting data from an output signal of the detector module 14. The counting data includes a detection position, an energy value, and a detection time of a gamma ray. For example, as described later, the counting data includes a scintillator number (P), an energy value (E), and a detection time (T). Although illustration is omitted in FIG. 1, the detector modules 14 are divided into blocks, and include the counting-data collecting circuitry 15 in each block. For example, when the single detector module 14 corresponds to one block, the counting-data collecting circuitry 15 is provided in each of the detector modules 14.

The console unit 20 accepts an operation of the PET apparatus 100 by a user, and controls imaging of a PET image, and reconstructs a PET image by using the counting data collected by the base unit 10. As shown in FIG. 1, the console unit 20 includes an input interface 21, a display 22, couch control circuitry 23, the memory 24, simultaneous counting-data generating circuitry 25, image reconstructing circuitry 26, system control circuitry 27, and correcting circuitry 28. The respective circuitries included in the console unit 20 are connected through a bus.

The input interface 21 is used to input various kinds of instructions and settings by a user of the PET apparatus 100. The input interface 21 transfers the input various kinds of instructions and settings to the system control circuitry 27. For example, the input interface 21 is used to input an imaging start instruction and an imaging end instruction. For example, the input interface 21 is implemented by a mouse, a keyboard, a button, a panel switch, a touch command screen, a foot switch, a trackball, a joystick, and the like.

The display 22 is implemented by a liquid crystal monitor, a cathode ray tube (CRT) monitor, a touch panel, and the like that is referred by a user. The display 22 displays a PET image, or a graphical user interface (GUI) to accept various instructions and settings from a user, under control of the system control circuitry 27.

The couch control circuitry 23 controls the couch driving circuitry 13. For example, the couch control circuitry 23 is implemented by a processor.

The memory 24 stores various kinds of data that are used in the PET apparatus 100. The memory 24 is implemented, for example, by a semiconductor memory device, such as a random access memory (RAN) and a flash memory, a hard disk, an optical disk, or the like.

The memory 24 stores a list of the counting data that is generated by the counting-data collecting circuitry 15. The list of the counting data stored in the memory 24 is used for processing performed by the simultaneous counting-data generating circuitry 25. The list of the counting data stored in the memory 24 can be deleted after it is used for processing by the simultaneous counting-data generating circuitry 25, or can be stored for a predetermined period.

FIG. 2 is a diagram for explaining a list of counting data according to the first embodiment. As shown in FIG. 2, the memory 24 stores the counting data including a scintillator number (P), an energy value (E), and a detection time (T), associating with a module identification (ID) to identify the detector module 14.

Furthermore, the memory 24 stores a chronological list of the simultaneous counting data that is generated by the simultaneous counting-data generating circuitry 25. Moreover, the chronological list of the simultaneous counting data stored by the memory 24 is used for processing performed by the image reconstructing circuitry 26. The chronological list of the simultaneous counting data stored in the memory 24 can be deleted after it is used for processing by the image reconstructing circuitry 26, or can be stored for a predetermined period.

FIG. 3 is a diagram for explaining the chronological list of the simultaneous counting data according to the first embodiment. As shown in FIG. 3, the memory 24 stores sets of counting data, associating with a coincidence number that is a serial number of the simultaneous counting data. In the chronological list of the simultaneous counting data, data is arranged substantially in chronological order based on the detection time (T) of the counting data.

Moreover, the memory 24 stores a PET image that is reconstructed by the image reconstructing circuitry 26. The PET image stored by the memory 24 is displayed on the display 22 by the system control circuitry 27. Furthermore, the memory 24 stores various kinds of programs.

Returning back to FIG. 1, the simultaneous counting-data generating circuitry 25 generates the chronological list of the simultaneous counting data by using a list of counting data that is generated by the counting-data collecting circuitry 15. For example, the simultaneous counting-data generating circuitry 25 searches a list of the counting data that is stored in the memory 24, for a set of counting data of a pair of gamma-rays that are counted substantially at the same time based on the detection time (T) of the counting data. Moreover, the simultaneous counting-data generating circuitry 25 generates simultaneous counting data per set of the counting data that is acquired as a result of the search, and stores the generated simultaneous counting data in the memory 24 while arranging the data in substantially chronological order.

For example, the simultaneous counting-data generating circuitry 25 generates the simultaneous counting data based on a condition (simultaneous-counting-data generation condition) for generating simultaneous counting data input by a user. The simultaneous-counting-data generation condition includes a time window width. For example, the simultaneous counting-data generating circuitry 25 generates simultaneous counting data based on the time window width.

For example, the simultaneous counting-data generating circuitry 25 refers to a list of counting data stored in the memory 24, and searches for a set of counting data, a time difference in the detection time (T) of which is within the time window width, among the detector modules 14. For example, finding a set of "P11, E11, T11" and "P22, E22, T22" as a set satisfying the simultaneous-counting-data generation condition, the simultaneous counting-data generating circuitry 25 generates simultaneous counting data with this set, and stores it in the memory 24. The simultaneous counting-data generating circuitry 25 can generate the simultaneous counting data by using an energy window width together with the time window width. Moreover, the simultaneous counting-data generating circuitry 25 can be arranged in the base unit 10.

The image reconstructing circuitry 26 reconstructs a PET image. For example, the image reconstructing circuitry 26 reads the chronological list of simultaneous counting data that is stored in the memory 24, and reconstructs a PET image by using the read chronological list. Furthermore, the image reconstructing circuitry 26 stores the reconstructed PET image in the memory 24. For example, the image reconstructing circuitry 26 is implemented by a processor.

The system control circuitry 27 performs overall control of the PET apparatus 100 by controlling the base unit 10 and the console unit 20. For example, the system control circuitry 27 controls imaging in the PET apparatus 100. For example, the system control circuitry 27 is implemented by a processor.

The correcting circuitry 28 includes a first identifying function 28a, a second identifying function 28b, and a correcting function 28c. The first identifying function 28a, the second identifying function 28b, and the correcting function 28c, which are components of the correcting circuitry 28 shown in FIG. 1 are recorded in the memory 24 in a form of a computer-executable program. The correcting circuitry 28 is a processor that reads respective programs from the memory 24, and executes the read programs, thereby implementing functions corresponding to the respective reprograms. In other words, the correcting circuitry 28 that has read the respective programs is to have the respective functions shown in the correcting circuitry 28 in FIG. 1. The first identifying function 28a, the second identifying function 28b, and the correcting function 28c are described later.

Note that a term "processor" used in the above explanation signifies, for example, a central processing unit (CPU), a graphics processing unit (GPU), or a circuitry such as an application specific integrated circuit (ASIC), a programmable logic device (SPLD), a complex programmable logic device (CPLD), and a field programmable gate array (FPGA). The processor implements a function by reading and executing a program stored in the memory 24. Instead of storing the program in the memory 24, it can be configured to install the program directly in a circuitry of the processor. In this case, the processor reads the program installed in the circuitry, and executes the read program, thereby implementing the function. The respective processors of the present embodiment are not limited to be configured as single circuitry per processor, but can be configured as one processor by combining multiple independent circuitries to implement the function.

The overall configuration of the PET apparatus 100 according to the first embodiment has been explained above.

Figure 4:
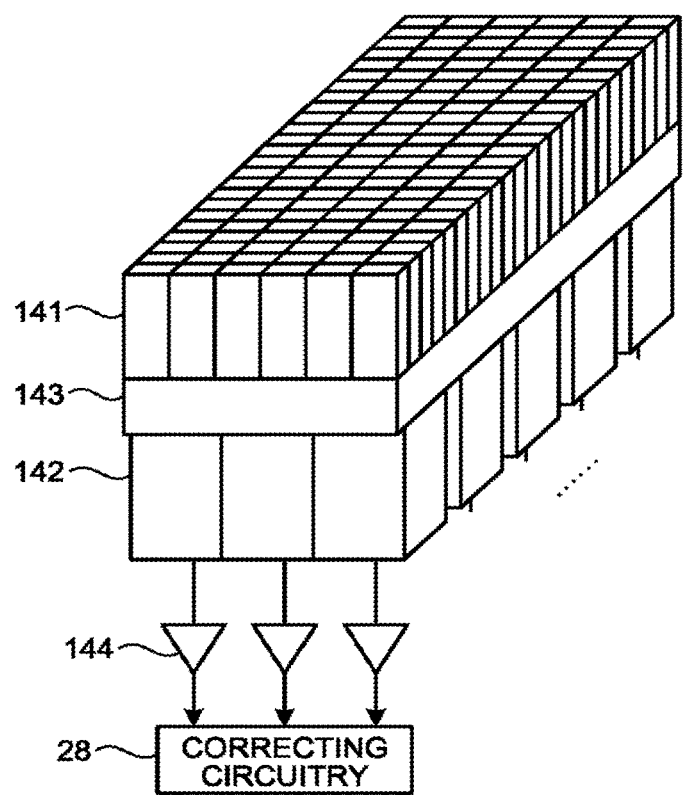
FIG. 4 shows one example of a configuration of a detector module according to the first embodiment.

Next, one example of a configuration of the detector module 14 according to the first embodiment is explained. FIG. 4 shows one example of a configuration of the detector module 14 according to the first embodiment. As shown in FIG. 4, the detector module 14 is an Anger detector of a photon-counting system, and includes plural scintillators 141, plural photomultiplier tubes (PMT) 142, a light guide 143, and plural amplifier circuitries 144.

The scintillator 141 converts a pair of gamma rays radiated when a positron emitted inside the subject P is coupled with an electron and pair-annihilated into scintillation photons (optical photons), and outputs the scintillation photons. For example, when one gamma ray enters, the scintillator 141 outputs one scintillation photon. The scintillator 141 is formed, for example, with a scintillator crystal, such as lanthanum bromide (LaBr3), lutetium yttrium oxyorthosilicate (LYSO), lutetium oxyorthosilicate (LSO), and lutetium gadolinium oxyorthosilicate (LGSO). As shown in FIG. 4, the scintillator 141 is arranged two-dimensionally.

The photomultiplier tube 142 converts the scintillation photon output from the scintillator 141 into an electrical signal. As shown in the example in FIG. 4, multiple units of the photomultiplier tubes 142 are arranged. The photomultiplier tube 142 has a photocathode that receives a scintillation photon and generates a photoelectron, multiple layers of dynodes that gives an electric field that accelerates the generated photoelectron, and an anode that is where an electron flows out. The electron emitted from the photocathode by the photoelectric effect is accelerated toward the dynode to collide against a surface of the dynode, and emits multiple electrons. This phenomenon is repeated over the multiple layers of dynodes, thereby multiplying the number of electrons in an avalanche process, and the number of electrons at the cathode reaches several millions. In the example, the gain factor of the photomultiplier tube 142 is several millions fold. For example, when a single scintillation photon enters the photomultiplier tube 142, the photomultiplier tube 142 outputs an electrical signal constituted of several millions of electrons. Moreover, as it is the multiplication using the avalanche phenomenon, a voltage equal to or higher than 1000 volts is usually applied between the dynode and the cathode. The photomultiplier tube 142 is one example of a converter.

The light guide 143 transmits the scintillation photon output from the scintillator 141 to the photomultiplier tube 142. The light guide 143 is formed, for example, using a plastic material having an excellent optical transmittance, and the like.

As described, the detector module 14 converts a pair-annihilation gamma ray emitted from the inside of the subject P into a scintillation photon by the scintillator 141, and converts the scintillation photon obtained by the conversion into an electrical signal by the photomultiplier tube 142 to output. That is, the detector module 14 is an indirect conversion detector.

The detector module 14 calculates a position of the scintillator 141 that has output light, by performing barycenter calculation of an output of the photomultiplier tubes 142 to which light has entered. Such a logic of calculating a position of the scintillator 141 is called, for example, Anger logic. When a position of the scintillator 141 is calculated by the logic, although the number of the photomultiplier tubes 142 can be less than the number the scintillators 141, it is necessary to identify the position of the scintillator 141 from coordinates acquired as a result of the barycenter calculation.

The respective amplifier circuitries 144 are connected to a subsequent position to the respective photomultiplier tubes 142. The amplifier circuitry 144 amplifies an electrical signal output from the photomultiplier tube 142 by a predetermined amplification factor, to output to the correcting circuitry 28.

The gain factor of the photomultiplier tube 142 described above is unique to each of the photomultiplier tubes 142. Therefore, for example, even when the same number of scintillation photons are input to the photomultiplier tubes 142, the signal intensity of electrical signals output therefrom is to take a unique value to each of the photomultiplier tubes 142, and there is a case that all of the signal intensities are not substantially the same. Therefore, energy calibration to adjust the amplification factor of the respective amplifier circuitries 144 is performed so that the signal intensities of electrical signals output from the respective amplifier circuitries 144 are substantially the same when the same number of scintillation photons are input to the respective photomultiplier tubes 142.

In the energy calibration described above, as a signal intensity of an electrical signal output from each of the photomultiplier tube 142, a signal intensity as follows is used. For example, a histogram in which a horizontal axis is a signal intensity of an electrical signal, and a vertical axis is the number of events that is the number of incident pair-annihilation gamma rays, a signal intensity corresponding to the largest number of events is used. That is, for each of the photomultiplier tubes 142, a signal intensity of the peak in the histogram is used as a signal intensity of the electrical signal. In the energy calibration described above, the amplification factor of the respective amplifier circuitries 144 is adjusted so that the signal intensities of peaks in the histogram are substantially the same for all of the photomultiplier tubes 142.

As described, above, in the energy calibration, the signal intensity of a peak in the histogram is used for the respective photomultiplier tubes 142, accurate identification of the signal intensity of the peak leads to accurate energy calibration.

Details are described later, but if a scattered ray (scattered gamma ray) of a pair-annihilation gamma ray enters the scintillator 141 in addition to the pair-annihilation gamma ray, it becomes difficult to identify a peak of the histogram based only on pair-annihilation gamma rays accurately. Note that the histogram based only on pair-annihilation gamma rays signifies a histogram that is obtained from an electrical signal when only a pair-annihilation gamma ray enters the scintillator 141 out of a pair-annihilation gamma ray and a scattered gamma ray, and when a scintillation photon is converted into the electrical signal by the photomultiplier tube 142. Therefore, it is considered to perform the energy calibration described above by using a shielded discrete radio source or a shielded linear radio source of 68 Ge, or the like that radiates little-scattering monochromatic rays. In this case, for example, a maintenance period of about one week is provided besides a period of medical imaging of the subject P, and the energy calibration is performed using a period of about one day in this maintenance period. This energy calibration is performed, for example, once in three months. As described, the energy calibration is not performed for a relatively long period of time, and in addition, the gain factor of the photomultiplier tube 142 changes with time. Accordingly, the performance of the PET apparatus can be degraded for a relatively long time. Furthermore, such a maintenance period is a downtime in which medical imaging, which is the original purpose of the PET apparatus, cannot be performed. Therefore, providing the maintenance period can be a factor of reduction of the operational availability of the PET apparatus.

Therefore, in the first embodiment, to suppress reduction of the operational availability of the PET apparatus 100, and reduction of the performance of the PET apparatus for a long period of time, following processing is performed. Specifically, the PET apparatus 100 according to the first embodiment performs energy calibration by using an electrical signal that is obtained by medical imaging of the subject P, not performing the energy calibration by using a shielded discrete radio source or a shielded linear radio source in the maintenance period.

Figure 5:
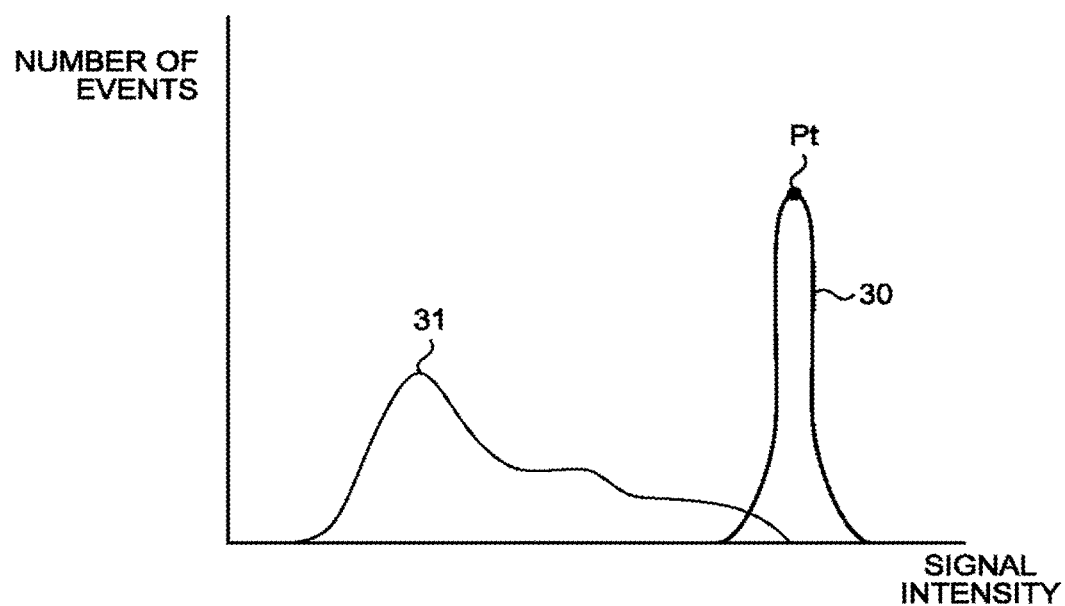
FIG. 5 shows one example of a histogram based on an electrical signal that is acquired by medical imaging.
Figure 6:
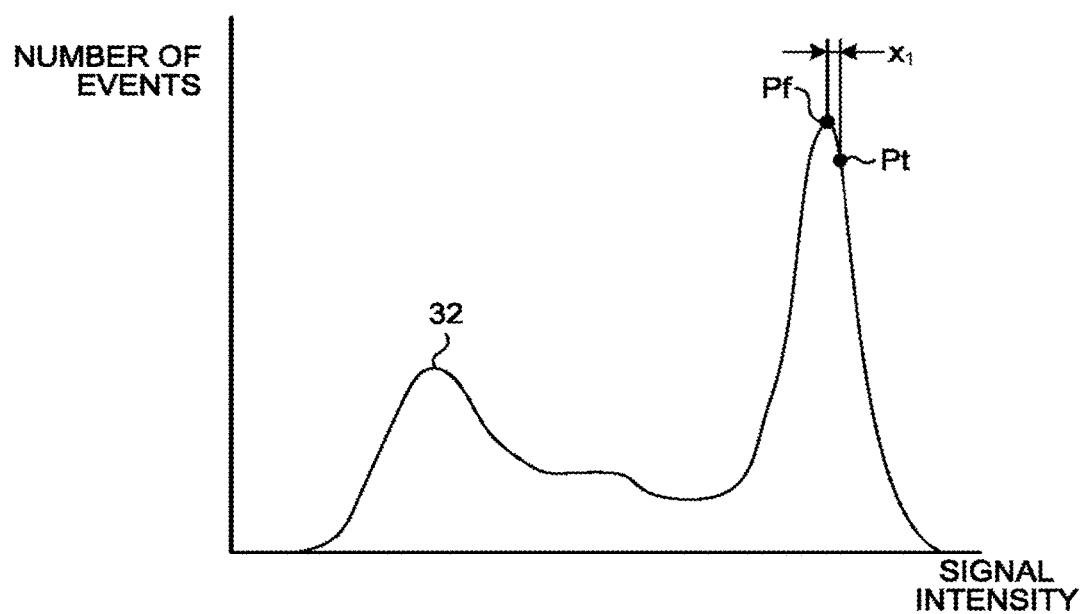
FIG. 6 shows one example of a histogram based on an electrical signal that is acquired by medical imaging.

However, from the subject P during the medical imaging, scattered rays of pair-annihilation gamma rays are radiated in addition to the pair-annihilation gamma rays. That is, the subject P is a radioactive ray source that causes scattering of photons. Therefore, in the medical imaging, the detector module 14 converts the scattered gamma rays, in addition to the pair-annihilation gamma rays, into scintillation photons, and outputs the scintillation photons into electrical signals to output. Accordingly, the histogram based on a pair-annihilation gamma ray and a scattered gamma ray radiated from the subject P is to be a histogram as explained below. FIG. 5 and FIG. 6 show one example of a histogram based on an electrical signal that is acquired by medical imaging. FIG. 5 and FIG. 6 show a histogram in which a horizontal axis is a signal intensity of an electrical signal, and a vertical axis is the number of events, which is the number of incident pair-annihilation gamma rays and scattered gamma rays. For example, the histogram based on a pair-annihilation gamma ray and a scattered gamma ray is to be a histogram 32 shown in the example in FIG. 6 obtained by combining a histogram 30 based on a pair-annihilation gamma ray and a histogram 31 based on a scattered gamma ray shown in the example in FIG. 5.

Note that the histogram based on a pair-annihilation gamma ray and a scattered gamma ray signifies a histogram that is obtained from an electrical signal when a pair-annihilation gamma ray and a scattered gamma ray enter the scintillator 141, and the pair-annihilation gamma ray and the scattered gamma ray are converted into scintillation photons by the scintillator 141, and the scintillation photons are converted into electrical signals by the photomultiplier tube 142. Similarly, the histogram based on a scattered gamma ray signifies a histogram that is obtained from an electrical signal when only a scattered gamma ray enters the scintillator 141 out of a pair-annihilation gamma ray and a scattered gamma ray, and the scattered gamma ray is converted into a scintillation photon by the scintillator, and the scintillation photon is converted into an electrical signal by the photomultiplier tube 142.

Generally, gamma rays lose energy when scattering. Therefore, the energy of scattered gamma ray is lower than the energy of a pair-annihilation gamma ray. Therefore, as can be seen in FIG. 5 and FIG. 6, the scattered gamma ray affects a shape of a portion of the histogram 30 on a lower intensity side relative to a peak Pt of the histogram 30 based on a pair-annihilation gamma ray. For example, as shown in the example in FIG. 6, due to the influence of the scattered gamma ray, the position of the peak Pt is shifted in a horizontal direction to a peak Pf by $x_1$. Therefore, in the energy calibration, when simply the peak Pf of a histogram based on an electrical signal obtained by medical imaging is identified, and the signal intensity of the peak Pf is used therefor, the accuracy of the energy calibration can be degraded.

Therefore, the PET apparatus 100 according to the first embodiment performs accurate energy calibration by identifying the signal intensity of a peak in a histogram based only on a pair-annihilation gamma ray out of a pair-annihilation gamma ray and a scattered gamma ray, by performing processing explained below.

Returning back to FIG. 1, the first identifying function 28a identifies the first signal intensity that is a signal intensity of a peak in a histogram that expresses the relationship between a signal intensity of an electrical signal output from the photomultiplier tube 142 and the number of incident gamma rays, for each of the photomultiplier tubes 142. The incident gamma ray is a gamma ray that enters the scintillator 141, for example. The incident gamma ray includes a pair-annihilation gamma ray and a scattered gamma ray.

For example, the first identifying function 28a first calculates a signal intensity of an electrical signal that is output from the photomultiplier tube 142 per incident gamma ray, for each of the photomultiplier tubes 142, based on an electrical signal output from each of the photomultiplier tubes 142 in medical imaging of the subject P. Subsequently, the first identifying function 28a creates a histogram that expresses a relationship between a signal intensity and the number of incident gamma rays by using the calculated signal intensity per incident gamma ray for each of the photomultiplier tubes 142. For example, the first identifying function 28a creates the histogram 32 as shown in the example in FIG. 6 for one of the photomultiplier tubes 142.

Figure 7:
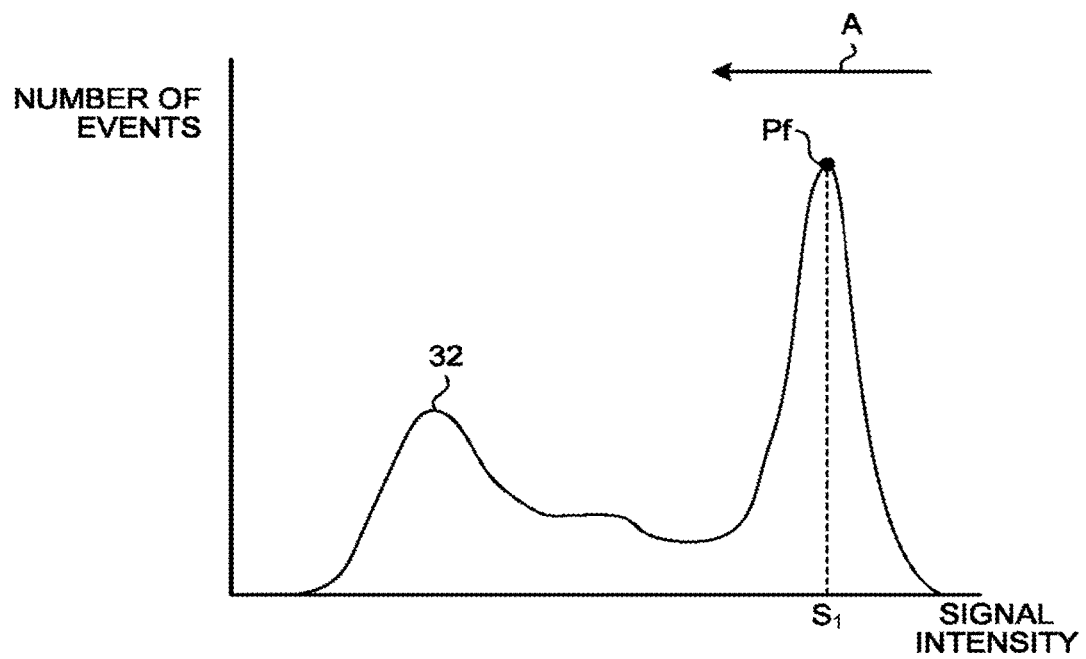
FIG. 7 shows one example of processing that is performed by a first identifying function according to the first embodiment.

Furthermore, the first identifying function 28a calculates a differential coefficient at each point in a histogram while sequentially moving a point on the histogram from a high intensity side to a low intensity side of the signal intensity, for each histogram. FIG. 7 is a diagram for explaining one example of processing that is performed by the first identifying function 28a according to the first embodiment. For example, when creating the histogram 32 as shown in the example in FIG. 6 for one of the photomultiplier tubes 142, the first identifying function 28a calculates a differential coefficient at each point in the histogram 32 while moving a point in a direction indicated by an arrow A as shown in the example in FIG. 7. The first identifying function 28a identifies a point when the differential coefficient first becomes 0 among differential coefficients sequentially calculated from the high intensity side, as a peak of the histogram based on a pair-annihilation gamma ray and a scattered gamma ray. That is, the first identifying function 28a identifies a point at which the differential coefficient first becomes 0 from the high intensity side to the low intensity side of the signal intensity in the histogram based on a pair-annihilation gamma ray and a scattered gamma ray, as the peak. For example, as shown in the example in FIG. 7, the first identifying function 28a identifies a point Pf when the differential coefficient first becomes 0 as the peak Pf of the histogram 32.

The first identifying function 28a can calculate the differential coefficient while moving a point on a histogram in a range in which the number of events is larger than a predetermined threshold from the high intensity side to the low intensity side of the signal intensity. Thus, it is possible to prevent the first identifying function 28a from identifying, as a peak by mistake, a point at which the differential coefficient has become 0 as a result of a shape being deformed due to an influence of a noise in a portion of the histogram that is affected by such a noise that the number of events becomes smaller than the predetermined threshold.

The first identifying function 28a then identifies the signal intensity of the identified peak as the first signal intensity. For example, as shown in the example in FIG. 7, the first identifying function 28a identifies a signal intensity $S_1$ of the peak Pf as a first signal intensity $S_1$.

The second identifying function 28b identifies the second signal intensity that is a signal intensity corresponding to energy of a pair-annihilation gamma ray, which is a gamma ray that has entered without scattering, in a histogram based on a portion of the histogram on a higher intensity side relative to the first signal intensity, for each of the photomultiplier tubes 142.

For example, the second identifying function 28b first identifies multiple relationships between a signal intensity and the number of events in a portion of the histogram on the high intensity side relative to the first signal intensity, for each of the photomultiplier tubes 142.

Figure 8:
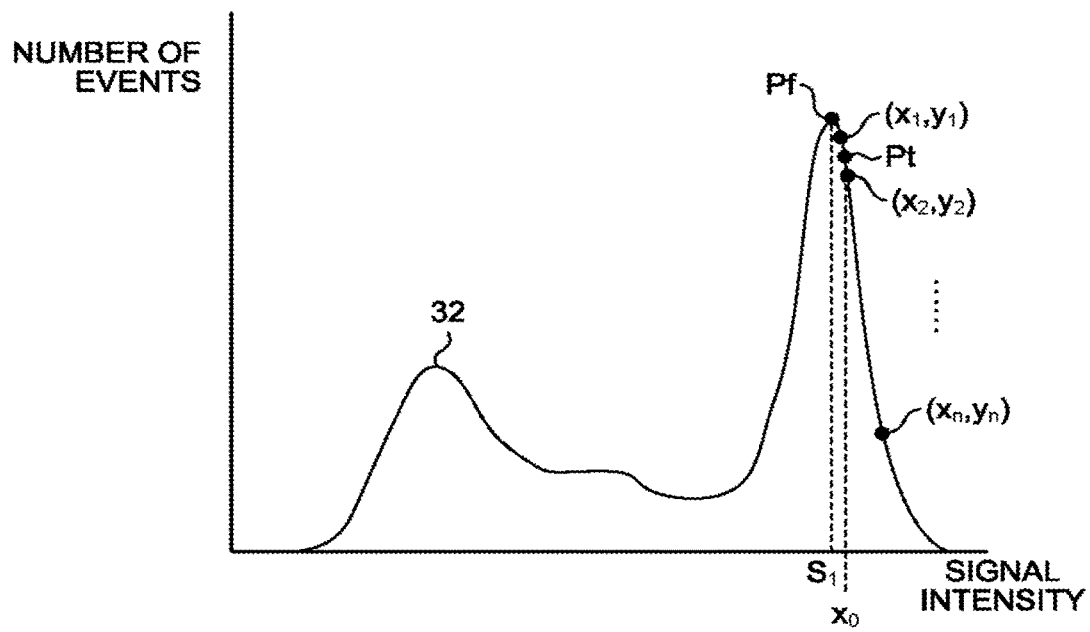
FIG. 8 is a diagram for explaining one example of processing that is performed by a second identifying function according to the first embodiment.

FIG. 8 is a diagram for explaining one example of processing that is performed by the second identifying function 28b according to the first embodiment. For example, as shown in the example in FIG. 8, the second identifying function 28b identifies n pieces of $(x_1, y_1)$, $(x_2, y_2)$, ..., $(x_n, y_n)$ as a relationship between a signal intensity and the number of events in a portion of the histogram 32 on the higher intensity side relative to the first signal intensity $S_1$, for one of the photomultiplier tubes 142. $x_1, x_2, \ldots, x_n$ are signal intensities. Moreover, $y_1, y_2, \ldots, y_n$ are the numbers of events corresponding to $x_1, x_2, \ldots, x_n$, respectively. In the following explanation, when it is not necessary to distinguish each of the signal intensities, "x" is used as a signal intensity. Similarly, when it is not necessary to distinguish each of the numbers of events, "y" is used as the number of events.

The second identifying function 28b identifies a signal intensity of a peak in a histogram based only on a pair-annihilation gamma ray out of a pair-annihilation gamma ray and a scattering gamma ray, by using the identified relationships between a signal intensity and the number of events. The histogram based only on a pair-annihilation gamma ray is assumed to be approximated to a Gaussian curve having a half-value breadth that is inversely proportional to a square root of the number of scintillation photons. Therefore, the second identifying function 28b performs curve fitting using n pieces of $(x_1, y_1)$, $(x_2, y_2)$, ..., $(x_n, y_n)$, to calculate an approximate curve that is approximated to the Gaussian curve, thereby identifying a signal intensity of a peak in the histogram based only on a pair-annihilation gamma ray.

One example of a method of identifying such a signal intensity of a peak is explained. For example, the Gaussian curve is expressed by Equation (1) below.

$$y = A e^{-((x-x_0)/\sigma)^2} \quad (1)$$

In Equation (1), A indicates an amplitude of a Gaussian function, σ indicates a standard deviation, and $x_0$ indicates a center of the Gaussian function. By transforming Equation (1), Equation (2) below is obtained.

$$x_0 + \sigma(\ln(y/A))^{1/2} = x \quad (2)$$

The second identifying function 28b calculates fitting parameters A, σ, and $x_0$ by substituting n pieces of $(x_1, y_1)$, $(x_2, y_2)$, ..., $(x_n, y_n)$ in Equation (2), thereby calculating a curve approximated to the Gaussian curve. The second identifying function 28b then identifies the calculated $x_0$ as the signal intensity of a peak in the histogram based only on a pair-annihilation gamma ray. That is, the second identifying function 28b calculates $x_0$ as the second signal intensity.

The second identifying function 28b uses a portion of the histogram on the higher intensity side relative to the first signal intensity, not using a portion of the histogram on the lower intensity side relative to the first signal intensity, when identifying a signal intensity of a peak in the histogram based only on a pair-annihilation gamma ray. As described above, while the portion of the histogram on the lower intensity side relative to the first signal intensity has been affected by scattered gamma rays to have the shape deformed, the portion of the histogram on the higher intensity side is assumed not to be affected by the scattered gamma rays. Therefore, the second identifying function 28b can identify a signal intensity of a peak corresponding to an energy value (511 keV) of a pair-annihilation gamma ray accurately, by using only the portion not affected by the scattered gamma ray.

Figure 9:
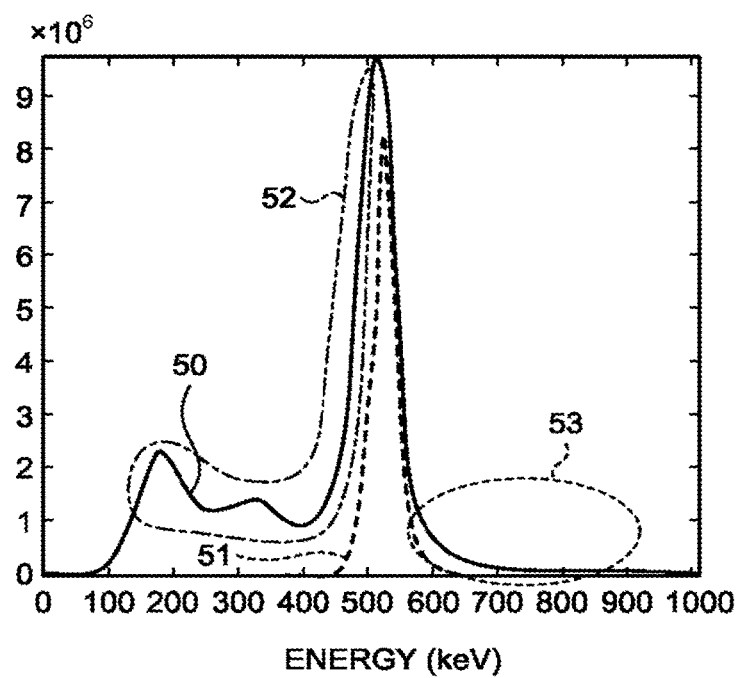
FIG. 9 is a diagram for explaining a case in which the second identifying function according to the first embodiment takes influence of pileup into account when identifying a signal intensity of a peak.

Note that the second identifying function 28b can take an influence of pileup into account at the time of identifying a signal intensity of a peak. One example of pileup is explained. For example, the photomultiplier tube 142 receives a scintillation photon output from the scintillator 141, and converts the received scintillation photon into an electrical signal to output it. However, when a next scintillation photon output from the scintillator 141 is received before the electrical signal is attenuated, the photomultiplier tube 142 converts this scintillation photon into an electrical signal, and outputs the electrical signal obtained by conversion, adding to the electrical signal derived from the scintillation photon received first to output. That is, the photomultiplier tube 142 outputs a single electrical signal having high signal intensity in which electrical signals derived respectively from multiple scintillation photons. Such a single electrical signal with high signal intensity is an electrical signal corresponding to a single gamma ray. A phenomenon in which only an electrical signal that corresponds to a single gamma ray is output from the detector module 14 even though multiple gamma rays have entered the detector module 14 is called pileup. For example, as the time interval of gamma rays to enter the detector module 14 becomes shorter, the probability of occurrence of pileup increases. FIG. 9 is a diagram for explaining a case in which the second identifying function 28b according to the first embodiment takes influence of pileup into account when identifying a signal intensity of a peak. The example in FIG. 9 shows a histogram 50 based on a pair-annihilation gamma ray and a scattered gamma ray, and a histogram 51 based only on a pair-annihilation gamma ray, in which a horizontal axis is energy corresponding to a signal intensity, and a vertical axis is the number of events. As described above, a portion 52 surrounded by an alternate long and short dashed line on a lower intensity side relative to a peak of the histogram 50 based on an electrical signal that is obtained by medical imaging of the subject P can be affected by pileup.

In a portion 53, the signal intensity becomes high due to occurrence of pileup. Therefore, compared to the histogram 51, the portion 53 of the histogram 50 is deformed such that the signal intensity increases. The occurrence frequency of this pileup is determined according to the number (count rate) of incident gamma rays per unit time. If the count rate is grasped, it is possible to estimate how much the signal intensity (or energy corresponding to a signal intensity) is increased to be high compared to the histogram 51.

Therefore, the second identifying function 28b calculates a count rate, and estimates how much the signal intensity (or energy corresponding to a signal intensity) has increased in the portion 53 to be high compared to the histogram 51 based on the calculated count rate. Furthermore, the second identifying function 28b corrects the histogram 50 such that the signal intensity (or energy) is decreased by the estimated signal intensity (or energy) in the portion 53. The second identifying function 28b then identifies the second signal intensity with the corrected histogram 50 by the method described above. That is, the second identifying function 28b performs correction to remove the influence of pileup from the histogram 50 based on the calculated count rate, and identifies the second signal intensity based on the corrected histogram 50. As described, the second identifying function 28b identifies the second signal intensity taking pileup into account. Thus, the second signal intensity can be identified further accurately.

The correcting function 28c corrects the signal intensity of electrical signals output from the respective photomultiplier tubes 142 based on the second signal intensity identified for each of the photomultiplier tubes 142 by performing the energy calibration described above.

For example, the correcting function 28c calculates a signal intensity of an electrical signal that can be output from all of the amplifier circuitries 144 as a target signal intensity, based on the width of the amplification factor of the amplifier circuitry 144 and the signal intensity of an electrical signal output from the photomultiplier tube 142. For example, the correcting function 28c calculates a mean value of signal intensities of electrical signals output from the photomultiplier tubes 142 or the amplifier circuitries 144, as a target signal intensity.

Furthermore, the correcting function 28c calculates, for each of the amplifier circuitries 144, an addition amount or a reduction amount of the amplification factor, how much the amplification factor is to be increased or decreased from the current amplification factor so that the signal intensity of an electrical signal output from the amplifier circuitry 144 is the target signal intensity. The correcting function 28c transmits the calculated addition amount or reduction amount to the amplifier circuitry 144, for each of the amplifier circuitries 144. Thus, when receiving the addition amount, the amplifier circuitry 144 increases the amplification factor by the addition amount, and when receiving the reduction amount, decreases the amplification factor by the reduction amount. Thus, the signal intensities of electrical signal output from all the amplifier circuitries 144 become substantially the target signal intensity. As described, the correcting function 28c performs energy calibration.

Figure 10:
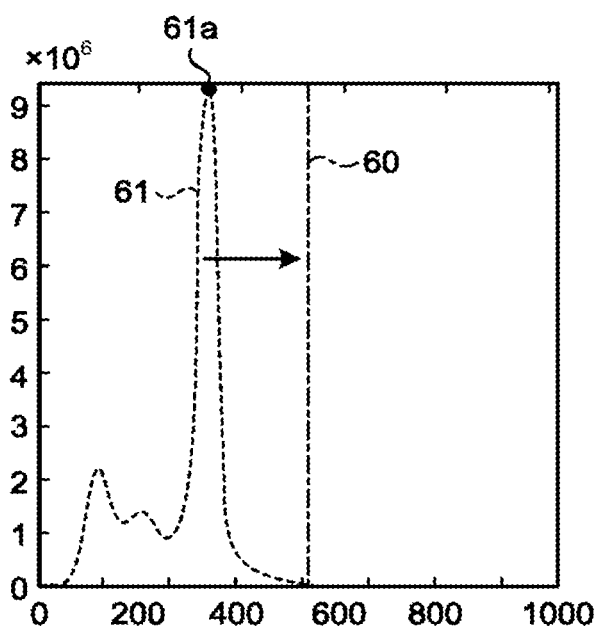
FIG. 10 is a diagram for explaining one example of processing that is performed by a correcting function according to the first embodiment.
Figure 11:
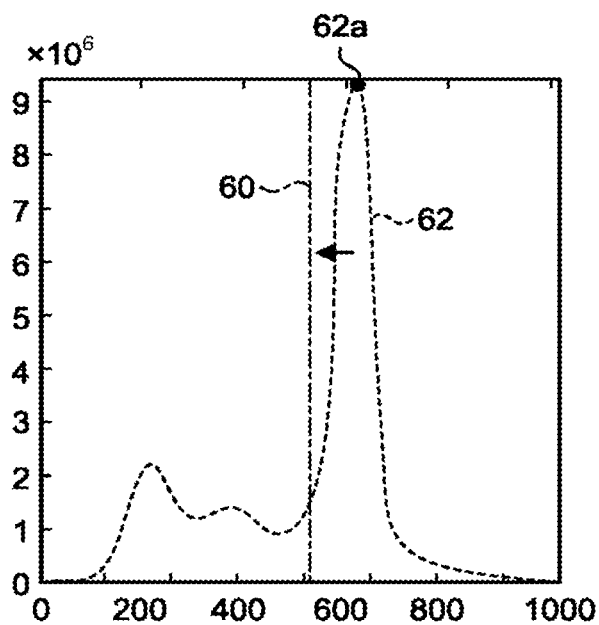
FIG. 11 is a diagram for explaining one example of processing that is performed by the correcting function according to the first embodiment.

FIG. 10 and FIG. 11 are diagrams for explaining one example of processing that is performed by the correcting function 28c according to the first embodiment. For example, as shown in the example n FIG. 10, the correcting function 28c calculates a target signal intensity 60. The correcting function 28c then calculates an addition amount of the amplification factor, how much the amplification factor should be increased from the current amplification factor so that the second signal intensity of a peak 61a in a histogram 61 for one of the multiplier tubes 142 becomes the target signal intensity 60. Subsequently, the correcting function 28c transmits the calculated addition amount to the corresponding amplifier circuitry 144.

Moreover, for example, as shown in the example in FIG. 11, the correcting function 28c calculates a reduction amount of the amplification factor, how much the amplification factor should be decreased from the current amplification factor so that the second signal intensity of a peak 62a in a histogram 62 for another one of the multiplier tubes 142 becomes the target signal intensity 60. Subsequently, the correcting function 28c transmits the calculated reduction amount to the corresponding amplifier circuitry 144.

Figure 12:
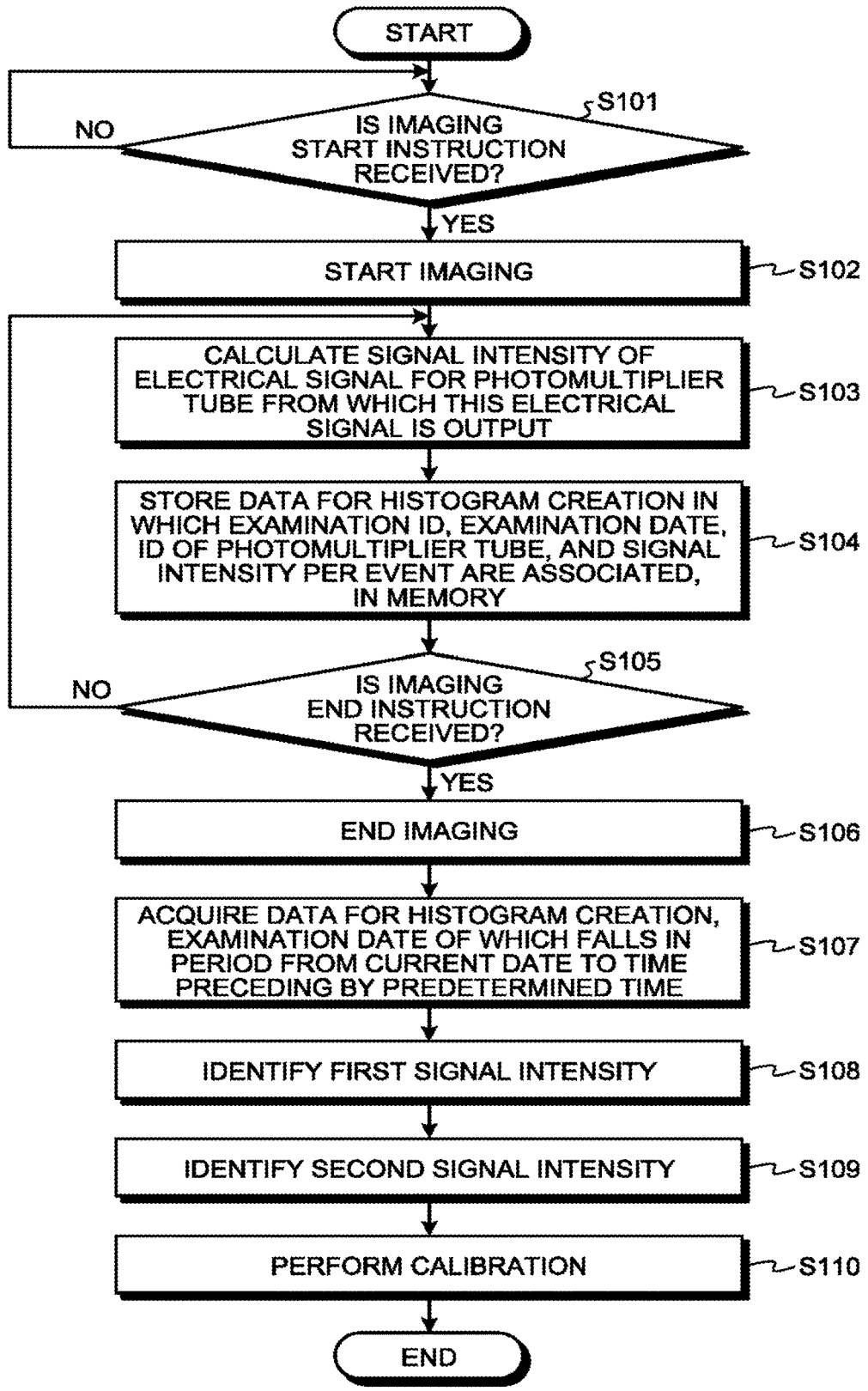
FIG. 12 is a flowchart showing one example of a flow of processing that is performed by the PET apparatus according to the first embodiment.

Next, one example of a flow of processing that is performed by the PET apparatus 100 according to the first embodiment is explained. FIG. 12 is a flowchart showing one example of a flow of the processing that is performed by the PET apparatus 100 according to the first embodiment.

As shown in the example in FIG. 12, the system control circuitry 27 determines whether an instruction (imaging start instruction) to start imaging in an examination of the subject P input by a user by operating the input interface 21 is received (step S101). When the imaging start instruction has not been received (step S101: NO), the system control circuitry 27 again determines whether an imaging start instruction is received at step S101.

On the other hand, when the imaging start instruction is received (step S101: YES), the system control circuitry 27 controls the base unit 10 to start imaging (step S102). For example, at step S102, the system control circuitry 27 controls the detector module 14 to start outputting an electrical signal based on a detected incident gamma ray. Moreover, at step S102, the system control circuitry 27 controls the counting-data collecting circuitry 15 to start generating counting data from the output signal of the detector module 14, and storing the generated counting data in the memory 24. Imaging started at step S102 is performed until it is ended at step S106 described later.

Subsequently, the first identifying function 28a of the correcting circuitry 28 calculates, for the photomultiplier tube 142 from which an electrical signal is output, a signal intensity of this electrical signal per event (step S103). The first identifying function 28a then stores data for histogram creation in which an examination ID that is an ID of this examination, a date of examination, an ID of the photomultiplier tube 142 that has output the electrical signal for which the signal intensity is calculated at step S103, and a signal intensity per event are associated with each other, in the memory 24 (step S104).

The system control circuitry 27 determines whether an instruction to end the imaging (imaging end instruction) that is input by the user by operating the input interface 21 is received (step S105). When the imaging end instruction has not been received (step S105: NO), the system control circuitry 27 returns to step S103, and calculates, for the photomultiplier tube 142 from which the electrical signal has been output, a signal intensity of this electrical signal per event. That is, during the imaging of the subject P, a signal intensity per event is calculated at step S103 and step S104, and data for histogram creation is generated.

On the other hand, when the imaging end instruction is received (step S105: YES), the system control circuitry 27 controls the base unit 10 to end the imaging (step S106). For example, at step S106, the system control circuitry 27 controls the detector module 14 to stop outputting an electrical signal based on a detected incident gamma ray. Moreover, at step S106, the system control circuitry 27 controls the counting-data collecting circuitry 15 to stop generating the counting data from an output signal from the detector module 14, and storing the generated counting data in the memory 24.

Subsequently, the first identifying function 28a acquires data for histogram creation, the date of examination of which falls in a predetermined period that is from a time predetermined time before a current date until the current date, out of the data for histogram creation stored in the memory 24 (step S107).

Subsequently, the first identifying function 28a creates a histogram for each of the photomultiplier tubes 142 by using the acquired data for histogram creation, and identifies the first signal intensity described above for each of the photomultiplier tubes 142 (step S108). As described above, the gain factor of the photomultiplier tube 142 changes with time. Therefore, there is a case in which the accuracy of the data for histogram creation that has been generated in a past examination performed at a preceding time to a point of time that is the predetermined time previous to the current date is low. Therefore, the first identifying function 28a creates a histogram without using the data for histogram creation when the accuracy can be low. Thus, it is possible to suppress degradation of the accuracy of a created histogram. As a result, degradation of the accuracy of the energy calibration can be suppressed.

At step S107, the data for histogram creation can be acquired only for the amount that the entire number of events is equal to or larger than a predetermined threshold. Thus, at step S108, the first identifying function 28a creates a histogram using the data for histogram creation corresponding to the number of events for which a histogram can be calculated accurately, and therefore, can create an accurate histogram.

The second identifying function 28b identifies the second signal intensity described above for each of the photomultiplier tubes 142 (step S109). The correcting function 28c then performs the energy calibration described above (step S110), and ends the processing.

As above, the PET apparatus 100 according to the first embodiment has been explained. The PET apparatus 100 identifies the second signal intensity of a peak in a histogram based only on a pair-annihilation gamma ray out of a pair-annihilation gamma ray and a scattered gamma ray, and uses the second signal intensity at the time of energy calibration. Therefore, according to the PET apparatus 100, the energy calibration can be performed accurately. That is, according to the PET apparatus 100, the intensities of electrical signals that are output from the photomultiplier tubes 142 can be uniform.

Furthermore, the PET apparatus 100 performs the energy calibration at each imaging. Therefore, the PET apparatus 100 is not required to perform the energy calibration, taking time of about one day during a maintenance period. Therefore, according to the PET apparatus 100, the reduction in the operational availability can be suppressed.

From the above, according to the PET apparatus 100, the energy calibration can be performed accurately while suppressing the reduction in the operational availability.

Moreover, the PET apparatus 100 performs the energy calibration each time of imaging as described above. Therefore, according to the PET apparatus 100, it is possible to suppress degradation of the performance for a long time.

Furthermore, the PET apparatus 100 performs energy calibration without using a shielded linear radio source, a shielded linear radio source, or the like. Therefore, according to the PET apparatus 100, it is possible to avoid making a user feel inconvenience of buying and storing a shielded discrete radio source, a shielded linear radio source, or the like.

Second Embodiment

In the first embodiment, the case in which the PET apparatus 100 performs energy calibration after imaging is finished has been explained. However, the PET apparatus 100 can perform during imaging also. Such an embodiment is explained as a second embodiment. In the second embodiment, like symbol is given to processing similar to that of the first embodiment, and explanation thereof is omitted in some cases.

Figure 13:
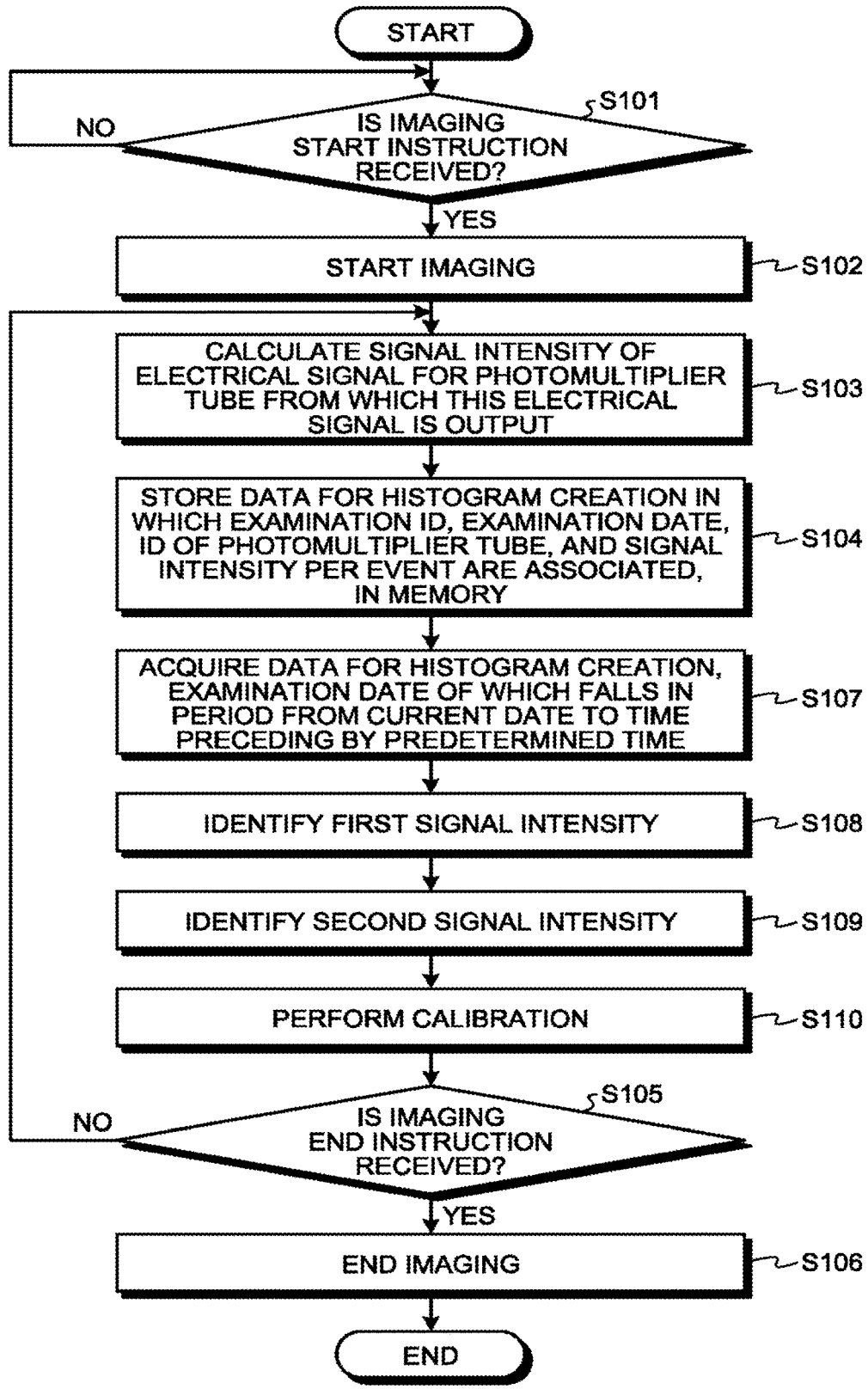
FIG. 13 is a flowchart showing one example of a flow of processing that is performed by a PET apparatus according to a second embodiment.

One example of a flow of processing that is performed by the PET apparatus 100 according to the second embodiment is explained. FIG. 13 is a flowchart showing one example of a flow of processing that is performed by the PET apparatus 100 according to the second embodiment.

The processing according to the second embodiment shown in FIG. 13 differ from the processing according to the first embodiment shown in FIG. 12 in a point that processing from step S107 to S110 is performed between step S104 and step S105.

In the second embodiment, the first identifying function 28a creates a histogram at step S108 each time an electrical signal is output by the photomultiplier tube 142, and identifies the first signal intensity. Furthermore, the second identifying function 28b identifies the second signal intensity at step S109 each time the first signal intensity is identified by the first identifying function 28a. Moreover, the correcting function 28c corrects a signal intensity of an electrical signal that is output from the respective photomultiplier tubes 142 by performing the energy calibration at step S110, each time the second signal intensity is identified by the second identifying function 28b. Thus, the PET apparatus 100 according to the second embodiment performs the energy calibration in real time during imaging. Therefore, the accuracy of counting data that is obtained by imaging can be further improved.

Third Embodiment

In the first embodiment and the second embodiment, the case in which a PET apparatus is used as the medical diagnostic-imaging apparatus has been explained. However, the first embodiment and the second embodiment can also be applied to a SPECT apparatus. It is because in the SPECT apparatus, the energy of a gamma ray can be determined based on a used nucleus, and a monochromatic X-ray is radiated. Therefore, in the third embodiment, a SPECT apparatus is explained as an example of the medical diagnostic-imaging apparatus to which what have been explained in the first embodiment and the second embodiment is applied. In the third embodiment, like symbols are assigned to components similar to those of the first embodiment and the second embodiment, and explanation thereof is omitted, or simplified in some case.

Figure 14:
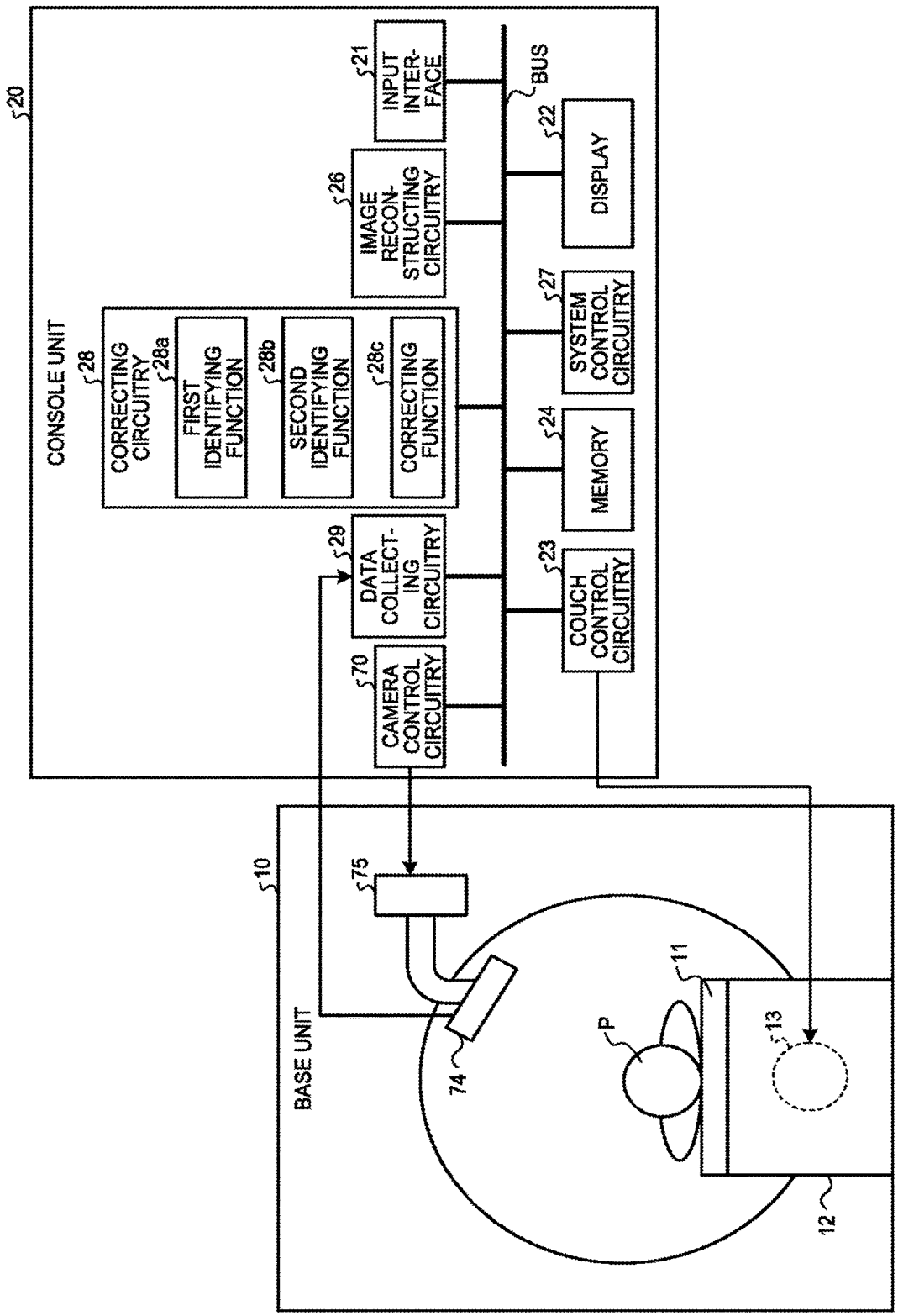
FIG. 14 shows one example of a configuration of a SPECT apparatus according to a third embodiment.

FIG. 14 shows one example of a configuration of a SPECT apparatus according to the third embodiment. The SPECT apparatus according to the third embodiment includes the base unit 10 and the console unit 20.

The base unit 10 is a device that collects projection data by detecting a gamma ray radiated from a radioactive medical product that is selectively taken into a living body tissue of the subject P. The base unit 10 includes the top plate 11, the couch 12, the couch driving circuitry 13, a gamma camera 74, and camera driving circuitry 75. The base unit 10 has a hollow to be an imaging opening as shown in FIG. 14.

The gamma camera 74 is a device that two-dimensionally detects an intensity distribution of a gamma ray that is radiated from a nucleus (radio isotope: RI) of a radioactive medical product that is selectively taken into a living body tissue of the subject P, and that generates projection data by subjecting the detected two-dimensional gamma-ray intensity-distribution data to, for example, amplification processing, and A/D conversion processing. The gamma camera 74 transmits the generated projection data to data collecting circuitry 29 described later.

The camera driving circuitry 75 is a device that moves the gamma camera 74 under control of camera control circuitry 70. For example, the camera driving circuitry 75 drives the gamma camera 74 along an inside of the imaging opening of the base unit 10. Thus, the gamma camera 74 rotates around the subject P and generates projection data in 360-degree direction.

The console unit 20 is a device that accepts an operation of the SPECT apparatus by a user, and that reconstructs a nuclear medical image (SPECT image) that is a tomogram in which a distribution in a body of the radioactive medical product that is given to the subject P is expressed from the projection data collected by the base unit 10.

The console unit 20 includes the input interface 21, the display 22, the couch control circuitry 23, the memory 24, the image reconstructing circuitry 26, the system control circuitry 27, the correcting circuitry 28, the data collecting circuitry 29, and the camera control circuitry 70. The respective circuitries included in the console unit 20 are connected through a bus.

The display 22 displays a SPECT image, or a GUI to accept various instructions and settings from a user through the input interface 21, under control of the system control circuitry 27.

The data collecting circuitry 29 collects the projection data transmitted from the gamma camera 74, and generates projection data subjected to correction processing, by performing correction processing such as logarithmic conversion, offset correction, and sensitivity correction, on each of the collected projection data. The data collecting circuitry 29 stores the generated projection data subjected to correction processing in the memory 24.

The image reconstructing circuitry 26 reads the projection data subjected to correction processing from the memory 24, and reconstructs a SPECT image by performing back projection processing on the read projection data subjected to correction processing (for example, projection data in 360-degree direction subjected to correction processing). The image reconstructing circuitry 26 stores the reconstructed SPECT image in the memory 24.

The system control circuitry 27 performs overall control of the SPECT apparatus by controlling an operation of the base unit 10 and the console unit 20. Specifically, the system control circuitry 27 controls the couch control circuitry 23 and the camera control circuitry 70, thereby executing the projection-data collection processing in the base unit 10. Moreover, the system control circuitry 27 controls the entire image processing in the console unit 20 by controlling the correction processing of the data collecting circuitry 29 and the reconstruction processing of the image reconstructing circuitry 26. Furthermore, the system control circuitry 27 controls to display a SPECT image stored in the memory 24 on the display 22.

The gamma camera 74 is configured including the detector module 14 explained in the first embodiment and the second embodiment. The scintillator 141 included in the detector module 14 converts a gamma ray that is radiated from an internal tissue of the subject P into a scintillation photon that has a peak in an ultraviolet region. The photomultiplier tube 142 included in the detector module 14 converts the scintillation photon input from the scintillator 141 into an electrical signal with a predetermined gain factor, and transmits this electrical signal to the correcting circuitry 28 according to the third embodiment. That is, the detector module 14 according to the third embodiment detects a gamma ray radiated from the inside of the subject P, and outputs an electrical signal based on the detected gamma ray.

The gamma camera 74 generates projection data from two-dimensional gamma-ray intensity-distribution data based on the electrical signal. The gamma camera 74 then transmits the generated projection data to the data collecting circuitry 29.

The correcting circuitry 28 according to the third embodiment performs processing similar to that of the correcting circuitry 28 according to the first embodiment, by using the electrical signal transmitted from the gamma camera 74.

As above, the SPECT apparatus according to the third embodiment has been explained. As described above, the correcting circuitry 28 according to the third embodiment performs processing similar to that of the correcting circuitry according to the first embodiment. According to the SPECT apparatus according to the third embodiment, an effect similar to that of the first embodiment can be obtained.

The first embodiment and the second embodiment have been explained with a PET apparatus as an example of the medical diagnostic-imaging apparatus, and the third embodiment has been explained with a SPECT apparatus as an example of the medical diagnostic-imaging apparatus. However, what has been explained in the first embodiment, the second embodiment, or the third embodiment can be applied to an X-ray computed tomography (CT) apparatus as the medical diagnostic-imaging apparatus also. For example, to an X-ray CT apparatus that is equipped with an X-ray source radiating a monochromatic X-ray, what has been explained in the first embodiment, the second embodiment, or the third embodiment can be applied. Moreover, even to an X-ray CT apparatus that is equipped with an X-ray source radiating multicolored X-ray, by using a peak corresponding to a characteristic X-ray, what has been explained in the first embodiment, the second embodiment, or the third embodiment can be applied. Furthermore, to a photon-counting X-ray CT apparatus, what has been explained in the first embodiment, the second embodiment, or the third embodiment can be applied. The detector modules included in such an X-ray CT apparatus include a scintillator that converts a radioactive ray that has passed through a subject and entered therein without scattering, and a scattered ray of the radioactive ray into a scintillation photon. That is, the detector modules output an electrical signal based on a radioactive ray that has passed through a subject and entered therein without scattering, and a scattered ray of the radioactive ray that has passed through the subject.

Furthermore, while in the first to the third embodiments, the case of using a photomultiplier tube has been explained, a silicon photomultiplier (SiPM) in which an avalanche photodiode (APD) that is not affected by a magnetic field is used as a semiconductor device array can be used instead of the photomultiplier tube.

Moreover, in the first to the third embodiments, the case in which the correcting circuitry 28 is provided in the console unit 20 has been explained. However, the correcting circuitry 28 can be provided in the base unit 10. Furthermore, without providing the correcting circuitry 28, a function similar to the function of the correcting circuitry 28 can be given to the counting-data collecting circuitry 15.

Furthermore, what has explained in the first to the third embodiments can be applied also when a scintillation photon from the single scintillator 141 enters the signal photomultiplier tube 142, or when a scintillation photon from the single scintillator 141 is distributed to the multiple photomultiplier tubes 142 to enter therein.

Moreover, in the first to the third embodiments, the case in which the first identifying function 28a creates a histogram that expresses a relationship between a signal intensity of an electrical signal output from the photomultiplier tube 142 and the number of incident gamma rays, and identifies the first signal intensity that is a signal intensity of a peak in the created histogram has been explained. However, the first identifying function 28a can identify the first signal intensity without creating such a histogram, but by using a relationship between a signal intensity of an electrical signal output from the photomultiplier tube 142 and the number of incident gamma rays. That is, the first identifying function 28a can identify the first signal intensity that is a signal intensity corresponding to a peak of the number of incident gamma rays, based on the relationship between a signal intensity of an electrical signal output from the photomultiplier tube 142 and the number of incident gamma rays, without creating a histogram.

Furthermore, while in the first to the third embodiments, the case in which the detector module 14 is an indirect conversion detector has been explained, it can be a direct conversion detector. For example, the detector module 14 can be a direct conversion detector that is constituted of a cadmium telluride (CdTe) semiconductor devices in a two-dimensional arrangement (for example, a semiconductor device of cadmium zinc telluride (CdZnTe)). The semiconductor device directly converts an incident pair-annihilation gamma ray into an electrical signal to output it. The detector module 14 constituted of such a semiconductor device outputs a one-pulse electrical signal (analog signal) each time when a pair-annihilation gamma ray enters therein.

Therefore, the detector module 14 outputs an electrical signal based on a pair-annihilation gamma ray that is emitted from the inside of the subject P when it is either an indirect conversion detector or a direct conversion detector.

According to the PET apparatus and the SPECT apparatus of at least one of the embodiments described above, energy calibration can be performed accurately while suppressing degradation of the operational availability.

The embodiments of the present invention have been explained, but these embodiments are presented as one example, and are not intended to limit the scope of the invention. These embodiments can be implemented in various other forms, and various omission, replacement, and alteration are allowed within a range not departing from the gist of the invention. These embodiments and modification thereof are included in the scope and the gist of the invention, and similarly, included in the scope of the invention described in claims and the scope of its equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic-imaging apparatus, comprising:
a plurality of converters, wherein each converter outputs an electrical signal based on incident radioactive rays; and
processing circuitry configured to
identify, for each converter of the plurality of converters, based on a functional relationship between a signal intensity of the electrical signal output from the converter and a number of the incident radioactive rays having the signal intensity, a first signal intensity corresponding to a peak of the functional relationship,
identify, for each converter of the plurality of converters, a second signal intensity corresponding to an energy of a radioactive ray that entered the converter without scattering, based on a portion of the functional relationship corresponding to an intensity higher than the identified first signal intensity, and
correct, for each converter of the plurality of converters, the signal intensity of the electrical signal output from the converter such that the second signal intensity identified for the converter matches a target signal intensity.

2. The medical diagnostic-imaging apparatus according to claim 1, wherein the processing circuitry is further configured to
identify, for each of the converters, the first signal intensity, which is a signal intensity of a peak in a histogram that expresses the functional relationship, and
identify, for each of the converters, the second signal intensity, which corresponds to the energy of the radioactive ray that entered the converter without scattering based on the portion of the histogram on a higher intensity side of the first signal intensity.

3. The medical diagnostic-imaging apparatus according to claim 2, wherein
the processing circuitry is further configured to identify the second signal intensity by performing curve fitting using the portion of the histogram on the higher intensity side of the first signal intensity.

4. The medical diagnostic-imaging apparatus according to claim 2, wherein
the processing circuitry is further configured to calculate a number of incident radioactive rays per unit time, perform correction on the histogram to exclude an influence of pileup from the histogram, based on the calculated number of incident radioactive rays per unit time, and identify the second signal intensity based on the histogram after correction.

5. The medical diagnostic-imaging apparatus according to claim 2, wherein
the processing circuitry is further configured to identify the second signal intensity by fitting the portion of the histogram on the higher intensity side relative of the first signal intensity to a Gaussian curve.

6. The medical diagnostic-imaging apparatus according to claim 2, wherein
the processing circuitry is further configured to identify, as the peak, a point at which a differential coefficient first becomes zero in the histogram from a high intensity side toward a low intensity side of a signal intensity.

7. The medical diagnostic-imaging apparatus according to claim 1, wherein
the processing circuitry is further configured to identify, for each converter of the plurality of converters, the first signal intensity by using the histogram, which is obtained from the electrical signal output from the converter during imaging of a subject.

8. The medical diagnostic-imaging apparatus according to claim 7, wherein the processing circuitry is further configured to, for each converter of the plurality of converters,
identify the first signal intensity each time the electrical signal is output by the converter,
identify the second signal intensity each time the first signal intensity is identified, and
correct the signal intensity of the electrical signal output from the converter, each time the second signal intensity is identified.

9. The medical diagnostic-imaging apparatus according to claim 1, wherein
the processing circuitry is further configured to identify, for each converter of the plurality of converters, the first signal intensity by using the functional relationship based on a signal intensity, per incident radioactive ray, of the electrical signal output from the converter in an examination executed in a predetermined period.

10. The medical diagnostic-imaging apparatus according to claim 1, wherein
each converter of the plurality of converters outputs the electrical signal based on the incident radioactive rays, which have radiated from a radiation source that causes scattering of photons and have entered the converter without scattering, and a scattered ray of a radioactive ray radiated from the radiation source.

11. The medical diagnostic-imaging apparatus according to claim 1, wherein
each converter of the plurality of converters outputs the electrical signal based on the radioactive rays, which are emitted from a subject and have entered the converter without scattering and a scattered ray of a radioactive ray emitted from the subject, or based on a radioactive ray that has passed through the subject and that has entered the converter without scattering and a scattered ray of a radioactive ray that has passed through the subject.

12. The medical diagnostic-imaging apparatus according to claim 1, wherein
the processing circuitry is further configured to adjust an amplification factor of amplifier circuitry connected in a subsequent stage of each converter of the plurality of converters, based on the second signal intensity identified for the converter.

13. The medical diagnostic-imaging apparatus according to claim 1, wherein
each converter of the plurality of converters outputs the electrical signal based on a pair of radioactive rays that are emitted when a positron that has been emitted inside a subject is coupled with an electron to be pair-annihilated.

14. The medical diagnostic-imaging apparatus according to claim 1, wherein
each convertor of the plurality of converters outputs the electrical signal based on the radioactive rays, which are output from an inside of a subject.

* * * * *